United States Patent
Matsushige et al.

(10) Patent No.: US 8,104,609 B2
(45) Date of Patent: Jan. 31, 2012

(54) CONTAINER

(75) Inventors: Koji Matsushige, Tokyo (JP); Masayuki Aizawa, Tokyo (JP); Nobutoshi Yamaguchi, Tokyo (JP); Ayumi Dodomi, Tokyo (JP)

(73) Assignee: Tokuyama Dental Corporation, Taito-Ku, Tokyo (JP)

( * ) Notice: Subject to any disclaimer, the term of this patent is extended or adjusted under 35 U.S.C. 154(b) by 275 days.

(21) Appl. No.: 12/073,659

(22) Filed: Mar. 7, 2008

(65) Prior Publication Data

US 2008/0217190 A1 Sep. 11, 2008

(30) Foreign Application Priority Data

Mar. 8, 2007 (JP) .................................. 2007-058744
May 22, 2007 (JP) .................................. 2007-135091

(51) Int. Cl.
*A61B 19/02* (2006.01)
*B65D 83/10* (2006.01)
*B65D 41/56* (2006.01)
*A47G 23/02* (2006.01)
(52) U.S. Cl. ........ 206/63.5; 206/368; 220/212; 248/150
(58) Field of Classification Search ................. 206/63.5, 206/349, 368, 372–379; 220/212, 268, 379, 220/380; 248/150, 164, 165, 310, 314, 346.06, 248/346.07, 346.3, 431, 429, 588
See application file for complete search history.

(56) References Cited

U.S. PATENT DOCUMENTS

| | | | | |
|---|---|---|---|---|
| 401,798 A | * | 4/1889 | Spencer | ........................ 472/115 |
| 565,435 A | * | 8/1896 | Crater | ........................ 108/157.1 |
| 1,778,175 A | * | 10/1930 | Thune | ................................ 47/71 |
| 3,598,271 A | * | 8/1971 | Holley | ........................... 215/227 |
| 3,637,563 A | | 1/1972 | Christena et al. | |
| 3,806,484 A | | 4/1974 | Dargan | |
| 4,084,517 A | * | 4/1978 | Guess | ...................... 108/158.12 |
| 4,208,072 A | * | 6/1980 | Iskendarian | ................ 297/440.1 |
| 4,275,815 A | * | 6/1981 | Davis | ............................. 206/508 |

(Continued)

FOREIGN PATENT DOCUMENTS

EP 0897710 A2 2/1999

(Continued)

OTHER PUBLICATIONS

Japanese Office Action dated Dec. 6, 2011 issued in the corresponding Japanese Patent Application No. 2007-058744.

*Primary Examiner* — J. Gregory Pickett
*Assistant Examiner* — Kaushikkumar Desai
(74) *Attorney, Agent, or Firm* — Buchanan Ingersoll & Rooney PC (57) ABSTRACT

A container which is not bulky at the time of shipping and can be stably stood on a suitable place. The container includes a lid member for closing a take-out opening (brittle portion) of the container body 2. On the lower outer side of the container body, there are formed slits for fitting the lid member to the container body after the container body and the lid member are separated apart, and auxiliary leg portions that protrude outward of the container body. The lid member is forming holding leg portions that protrude outward therefrom. Wing portions of the holding leg portions are inserted in the slits to fit the lid member to the container body, and the erected attitude of the container body is supported by the holding leg portions.

3 Claims, 10 Drawing Sheets

U.S. PATENT DOCUMENTS

| | | | |
|---|---|---|---|
| 4,291,811 A * | 9/1981 | Shaver | 211/205 |
| 5,150,804 A * | 9/1992 | Blanchet et al. | 220/212 |
| 5,395,862 A | 3/1995 | Neckers et al. | |
| 5,639,802 A | 6/1997 | Neckers et al. | |
| 5,744,511 A | 4/1998 | Kazama et al. | |
| 5,885,837 A | 3/1999 | Winkler et al. | |
| 6,372,313 B1 | 4/2002 | D'Alessio et al. | |
| 6,610,759 B1 | 8/2003 | Chappelow et al. | |
| 6,765,036 B2 | 7/2004 | Dede et al. | |
| 6,810,819 B2 * | 11/2004 | Kaniuk et al. | 108/25 |
| 6,930,134 B2 | 8/2005 | Suzuki et al. | |
| 7,021,486 B1 * | 4/2006 | Hurlbut | 220/379 |
| 2002/0154935 A1 | 10/2002 | Petrich et al. | |
| 2004/0186195 A1 | 9/2004 | Suzuki et al. | |
| 2004/0197730 A1 | 10/2004 | Rowe et al. | |
| 2005/0250868 A1 | 11/2005 | Suzuki et al. | |
| 2006/0154523 A1 | 7/2006 | Takahashi et al. | |
| 2006/0228159 A1 | 10/2006 | Phillips et al. | |
| 2007/0141267 A1 | 6/2007 | Sonnenschein et al. | |

FOREIGN PATENT DOCUMENTS

| | | |
|---|---|---|
| EP | 0927726 A1 | 7/1999 |
| EP | 1422254 A2 | 5/2004 |
| EP | 1431315 A2 | 6/2004 |
| EP | 1681032 A1 | 7/2006 |
| JP | 58-61744 U | 4/1983 |
| JP | 3-90866 U | 9/1991 |
| JP | 11-130945 A | 5/1999 |
| JP | 2003-175077 A | 6/2003 |
| JP | 2003-310646 A | 11/2003 |
| JP | 2004-196949 | 7/2004 |
| JP | 2006-193172 A | 7/2006 |

* cited by examiner

CONTAINER

BACKGROUND OF THE INVENTION

1. Field of the Invention

The present invention relates to a container in which the junction between an opening portion of a container body and a lid member is accomplished relying on a brittle portion, and the container body and the lid member can be separated away from each other by breaking the junction which is the brittle portion, the container capable of maintaining an erected attitude by using the lid member even if the container has such a shape which by itself cannot maintain the erected attitude.

2. Description of the Related Art

Adhesives for dental use can be grouped into those that are contained in a container designed for repetitive use a plurality of number of times and those that are contained in a container designed for use for the therapy of only one time. The former container designed for repetitive use a plurality of number of times contains the adhesive in an amount to meet the therapy of a plurality of number of times, and has its lid member opened for the therapy of every time. The latter container designed for containing the adhesive in an amount to meet the therapy of only one time is opened from its sealed state, and is, usually, discarded after each use irrespective of the amount of the adhesive that is remaining.

Figure 12:
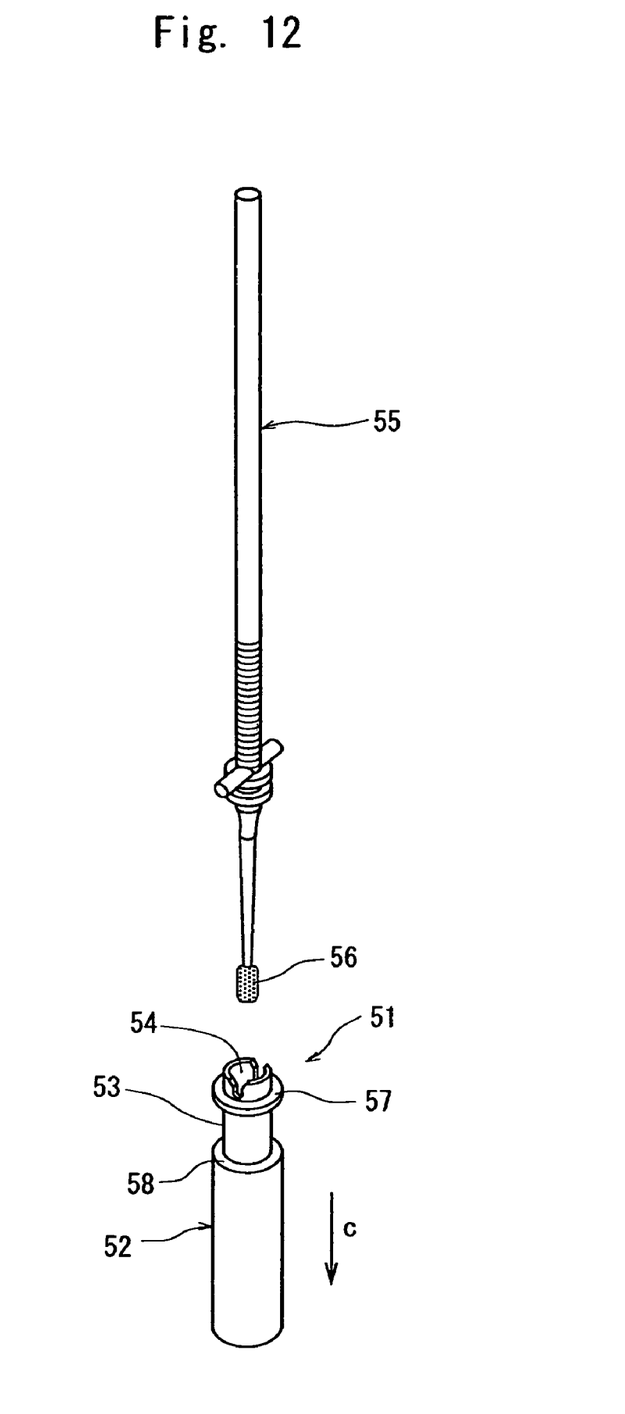
FIG. 12 is a perspective view of a conventional disposable container for an adhesive that has been used for the dental therapy.

FIG. 12 illustrates a conventional container for containing an dental adhesive for dental use.

A container 51 is constituted by a container body 52 and a lid member 53, the lid member 53 being fitted to the opening side of the container body 52 which is of a cylindrical shape having bottom. In a state that is illustrated, the container 51 is still unsealed. To take out the adhesive by opening the container 51, the lid member 53 is pushed into the container body 52 (direction of an arrow c) from the state that is shown until a flange 57 of the lid member 53 comes in contact with an upper end surface 58 of the container body 52. Then, due to the internal structure, a sealing portion (not shown) formed in the container 51 is unsealed, and an end 56 of a rod 55 is inserted in an opening 54 formed in an upper part of the lid member 53 to thereby take out the adhesive in a manner of being applied to the end portion 56. The container 51 is so constituted as cannot be returned back to the unsealed position shown in FIG. 1 once the lid member 53 is pushed into the container body 52. After the dental therapy has been finished, the container body 52 is discarded with the lid member 53 being inserted therein.

Figure 13:
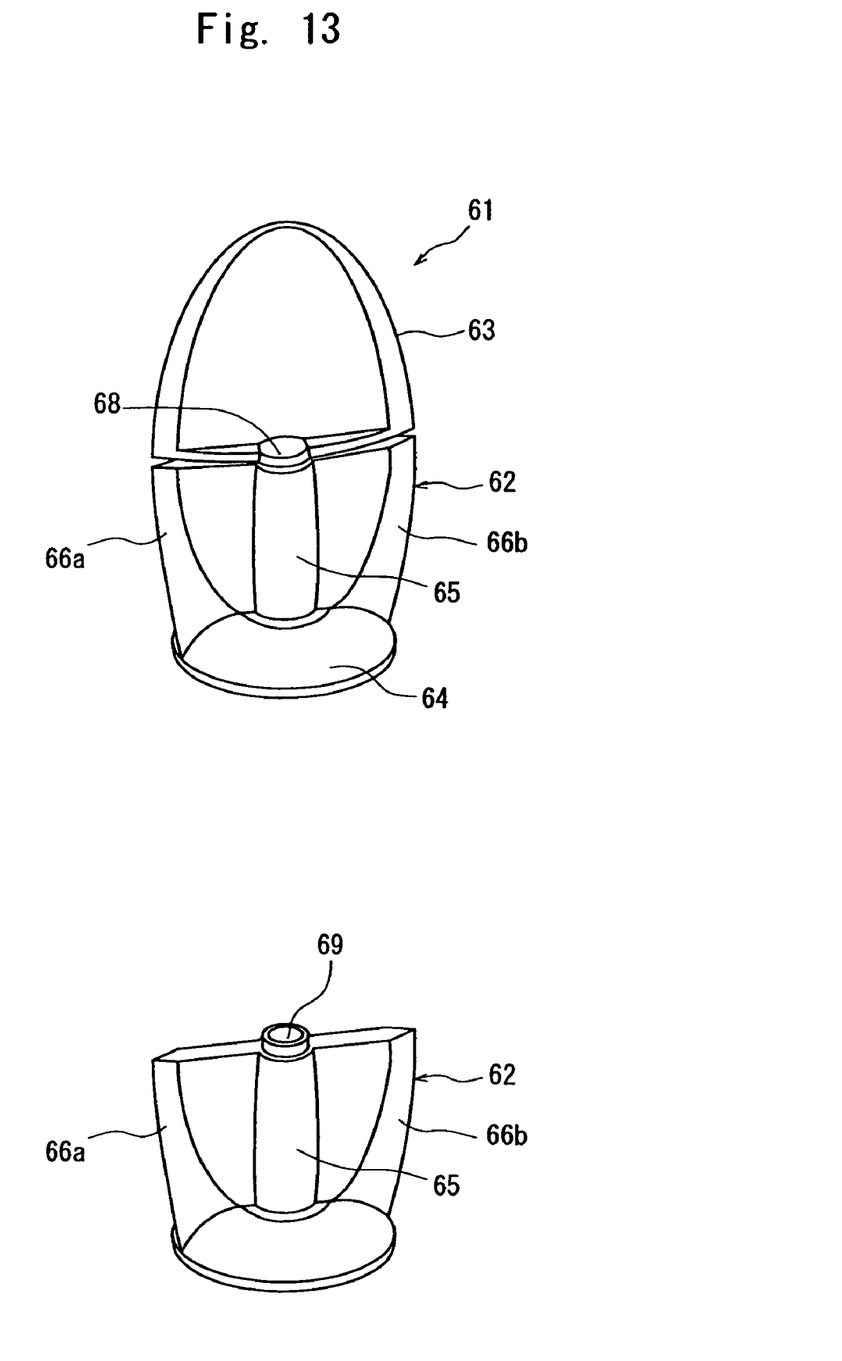
FIG. 13 is a perspective view of another conventional disposable container for an adhesive that has been used for the dental therapy.

FIG. 13A illustrates another conventional container for containing an adhesive for dental use.

A container 61 is constituted by a container body 62 and a lid member 63, and has a pedestal 64 of the shape of a disk at the lower part thereof. A container portion 65 is provided in the central portion so as to be erected upward in the up-and-down direction from the pedestal 64, and fins 66a and 66b of the shape of thin plates are formed on both the right and left sides of the container portion 65. Similarly, fins 66c and 66d of the shape of thin plates are also formed on both the right and left sides of the lid member 63. A brittle portion 68 is formed between the container body 62 and the lid member 63, the brittle portion 68 being bonded by melt-adhesion or the like method after the adhesive has been contained in the container portion 65.

To take out the adhesive by opening the container 61, the lid portion 63 is gripped and twisted so as to be cut the brittle portion 68. Referring next to FIG. 13B, the container body 62 is placed on a suitable position in an erected attitude, and a rod (see FIG. 4) is inserted in an opening 69 formed after the brittle portion 68 is cut off. Therefore, the adhesive is applied to the end of the rod so as to be used for the dental therapy. After the dental therapy has been finished, the container body 62 is discarded in a state of being separated away from the lid member 63.

Disposable containers for use of only one time have been disclosed in JP-A-2003-310646 and JP-A-2003-175077.

OBJECT AND SUMMARY OF THE INVENTION

With the container 51 shown in FIG. 12, the container body 52 and the lid member 53 remain integrally together even after the container 51 is opened. Therefore, the container 51 can be discarded without permitting them to be separated apart, which is an advantage. However, the container 51 as a whole is long in the longitudinal direction and loses stability when it is attempted to erect the container 51. Even if erected, the container 51 may easily fall down due to a slight swing of when the rod 55 is inserted in the container 51. Therefore, after the container 51 is opened, the dentist must continue the therapy by holding the container 51 by his one hand while holding the rod 55 by his other hand. When the therapy must be conducted by using the two hands, therefore, the dentist must have an assistant hold the container 51, which is inconvenient.

The container 61 shown in FIG. 13 is forming the pedestal 64 at the lower part of the container body 62 enabling the container body 62 to stand on a suitable place. Therefore, the dentist is allowed to hold a patient with his one hand and apply the adhesive to the patient by using his other hand, which is convenient for carrying out the operation. With this container 61, however, the container body 62 and the lid member 63 are separated from each other. After the therapy, therefore, the container body 62 and the lid member 63 are, in many cases, discarded in a state of being separated away from each other.

To stably stand the container body 62, further, the pedestal 64 is formed having a bottom surface very larger than the sectional area of the container body 62. These disposable dental adhesives are shipped being contained in a number of, usually, several hundred pieces (e.g., 500 pieces) in each casing. However, the pedestals 64 of a large size cause the containers 61 to become large in three-dimensional directions and, therefore, cause the casings to be shipped to become bulky.

The present invention was attained in view of the above circumstances, and has a first object of providing a container which is not bulky at the time of shipping, can be stably stood on a suitable place, and can be discarded without being separated into a container body and a lid member.

As described above, to unseal the container 61 shown in FIG. 13A, the fins 66a, 66b of the container body 62 and the fins 66c, 66d of the lid member 63 are turned in the opposite directions to cut the brittle portion 68 between the container body 62 and the lid member 63. The brittle portion 68 must have a strength of a certain degree since the content leaks out of the container body 62 if the lid member is broken. Further, at the time of cutting the lid member 63 from the container body 62, the brittle portion is not gradually broken but is entirely broken instantaneously enabling the lid member 63 to be separated away from the opening 69 of the container body 62.

However, since the breakage takes place between the hard resins, a slight shock (like snapping into two) is imparted to the container body 62 at the time of breaking. At this moment, the container body 62 and the lid member 63 may move relative to each other, whereby the opening 69 on the free end side of the container body 62 may swing to a large degree often causing the content to flow out from the opening due to the swinging motion.

Further, various methods can be contrived for joining the container body 62 and the lid member 63 together, such as heat-melt adhesion or using an adhesive. In any case, however, the container body 62 must be completely sealed to prevent the leakage of the content contained in the container body 62 yet enabling the container body 62 and the lid member 63 to be easily broken apart and, therefore, requiring a highly sophisticated junction technology.

The present invention was accomplished in view of the above circumstances and has a second object of providing a container which suppresses the opening 69 from swinging by suppressing the movement of the container body at the time when the junction portion between the container body and the lid member is broken, prevents the content from flowing out of the container body, and maintains the content in the container body in a sealed state even if the junction portion has not been completely sealed.

In order to solve the above first object, the present invention provides a container comprising a container body and a lid member for closing the container body, wherein the container body has, formed at one end portion thereof, an engaging portion for fitting the lid member to the container body, the lid member has, formed therein, a lid body for closing the container body and holding portions protruding outward beyond a body portion of the container body that contains the content therein, and after the container body and the lid member are separated apart, the lid member is fitted to the engaging portion to maintain the container body in an erected attitude by using the holding portions.

It is desired that auxiliary portions are so formed at a lower portion of the container body of the container as to protrude outward beyond the body portion of the container body, and the container body is maintained in an erected attitude by using the holding portions and the auxiliary portions.

The holding portions of the container are arranged in a number of two at positions facing each other on a straight line passing through the central portion of the lid body, the auxiliary portions are arranged in a number of two at positions facing each other on a straight line passing through the central portion of the container body, the holding portions and the auxiliary portions being arranged so as to pass on the same horizontal plane in a state where the container body is still unsealed, and the holding portions and the auxiliary portions being arranged nearly in a cross shape in a state where the lid body is fitted to the engaging portion of the container body.

It is, further, desired that the holding portions of the container are forming plate-like wing portions protruding outward of the lid member, and the engaging portion of the container body comprises slits which are so formed as to extend upward from the lower end of the container body, and the lid member is fitted to the container body by inserting the wing portions in the slits.

The container has three or more auxiliary portions and in a state where the container body is falling down, the height of the auxiliary portion at the highest position among the three or more auxiliary portions is lower than the maximum height of the body portion.

It is further desired that the lid member and the container body of the container are integrally coupled together at the take-out opening portion, the coupling being attained relying on a brittle portion that can be broken, and the content in the container body is an adhesive for dental (medical) use.

In order to achieve the above second object, the container of the present invention comprises a container body having an opening portion and a lid member coupled to the opening portion, wherein the opening portion of the container body and the lid member are joined together relying on a brittle portion, and the container body and the lid member are separated apart by breaking the junction portion which is the brittle portion, and wherein the lid member has a closing member at a portion thereof coupled to the container body, the closing member protruding into the container body, and the opening portion of the container body is closed by using the closing member.

The container is such that the lid member includes a cylindrical portion coupled to the opening portion and the closing member arranged in the inner circumferential portion of the cylindrical portion, and the closing member can be fitted into the cylindrical portion of the lid member.

The closing member of the container is made of an elastic member in such a manner that the outer circumferential surface thereof in cross section is larger than the inner circumferential surface of the cylindrical portion in cross section.

The lid member and the container body of the container can be joined together by heat-melt adhesion.

A grip portion can be formed on the container body of the container to protrude outward from the outer circumferential surface of the container body, a grip portion can be formed on the lid member to protrude outward from the outer circumferential surface of the lid member, and the cutting portion can be cut by turning the pair of grip portions in the opposite directions.

The content contained in the container body of the container may be an adhesive for medical use.

DETAILED DESCRIPTION OF PREFERRED EMBODIMENTS

The container according to the embodiments of the invention will now be described with reference to the drawings.

Figure 1:
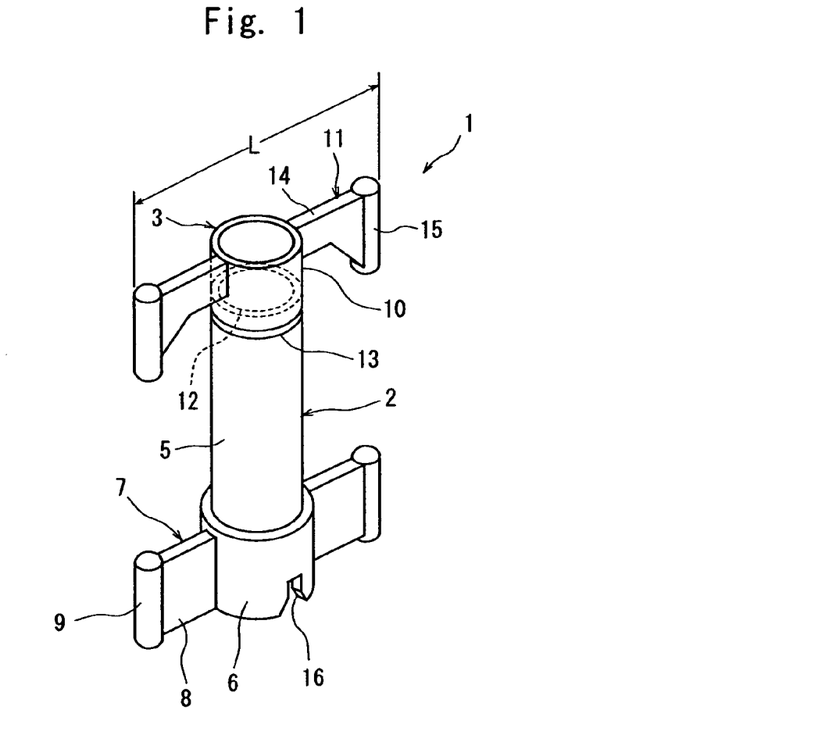
FIG. 1 is a perspective view of a container comprising a container body and a lid member according to a first embodiment of the invention in a state where the container has not been used yet.
Figure 2:
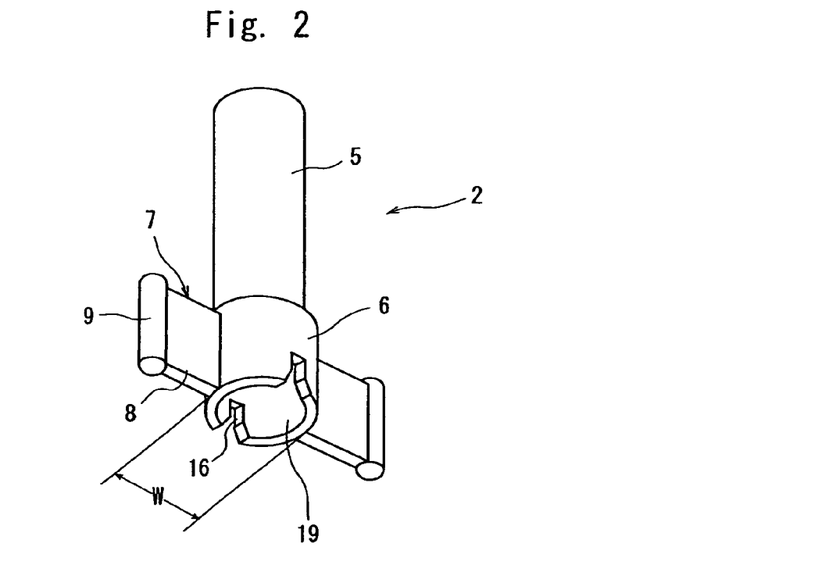
FIG. 2 is a perspective view of the container body in a state where the lid member is removed from the container body of the container of FIG. 1.

FIG. 1 illustrates a container for containing an adhesive for dental therapy in a state where the container has not been used yet, and FIG. 2 illustrates a container body 2.

The container 1 is a so-called disposable container for containing an adhesive for dental therapy. The container 1 made of a plastic material includes a container body 2 formed in the lower portion and a lid member 3 formed in the upper portion.

Of them, the container body 2 forms a body portion 5 in the upper portion thereof for containing an adhesive, and the body portion is of a cylindrical shape with bottom. In the lower portion of the body portion 5, a pedestal 6 is formed having a diameter larger than that of the body portion 5. Two auxiliary leg portions 7 are formed surrounding the pedestal 6, opposed to each other in the radial direction of the pedestal 6, protruding outwards in the direction of diameter, and facing the center of the pedestal 6. The auxiliary leg portions 7 include wing portions 8 coupled at the ends on one side to the pedestal 6 and cylindrical portions 9 coupled to the ends on the other side of the wing portions 8. The wing portions 8 are plate members of a square shape, and the upper ends of the cylindrical portions 9 are protruding beyond the upper ends of the wing portions 8.

The lid member 3 includes a lid body 10 and holding leg portions 11. The lid body 10 closes the interior of the container body 2 relying on a partitioning wall 12. The holding leg portions 11 are formed in a number of two surrounding the lid body 10, facing in the radial direction of the lid body 10 and protruding outward in the direction of diameter. The holding leg portions 11 include wing portions 14 coupled at the ends on one side to the lid body 10 and cylindrical portions 15 coupled to the ends on the other side of the wing portions 14. The positions where the holding leg portions 11 are formed are arranged on the same plane in which the holding leg portions 11 extend relative to a plane in which the auxiliary leg portions 7 of the container body 2 extend.

The container 1 is such that after the adhesive is contained in the container body 2, the container body 2 and the lid member 3 are air-tightly joined together by such closing means as melt-adhesion, and the junction portion is forming a brittle portion 13 having a thickness smaller than that of any other portions.

The pedestal 6 of the container body 1 is of a cylindrical shape having bottom with its lower side open. A pair of slits 16 is formed in the circumferential wall of the pedestal 6 extending upward from the lower end of the circumferential wall. The positions where the slits 16 are formed are arranged on a line at right angles with a line that connects the pair of auxiliary leg portions 7 passing through the center of the pedestal 6. Therefore, the auxiliary leg portions 7 and the slits 16 are alternately arranged in the circumferential direction of the pedestal 6 at an angle of 90 degrees. The width of the slit 16 is nearly equal to the thickness of the wing portion 14 of the holding leg portion 11.

An inner hole 19 is formed in the pedestal 6, the inner hole 19 having an inner diameter nearly equal to the outer diameter of the lid body 10 of the lid member 3. The lid member 3 that is separated from the container body 2 can be fitted into the inner hole 19 of the pedestal 6.

A dentist who is going to treat the teeth may use an adhesive contained in the above container. Namely, he may grip the container body 2 by his one hand, grip the holding leg portions 11 of the lid member 3 by his other hand, and may turn the container body 2 and the holding leg portions 11 in the opposite directions to cut the brittle portion 13. Upon cutting the brittle portion 13, the container body 2 forms an opening 17 for taking out the adhesive. Here, the holding leg portions 11 have a large distance L between the cylindrical portions 15 and 15 at both ends, and produces a large moment of rotation enabling the brittle portion 13 to be cut with a small force.

Figure 3:
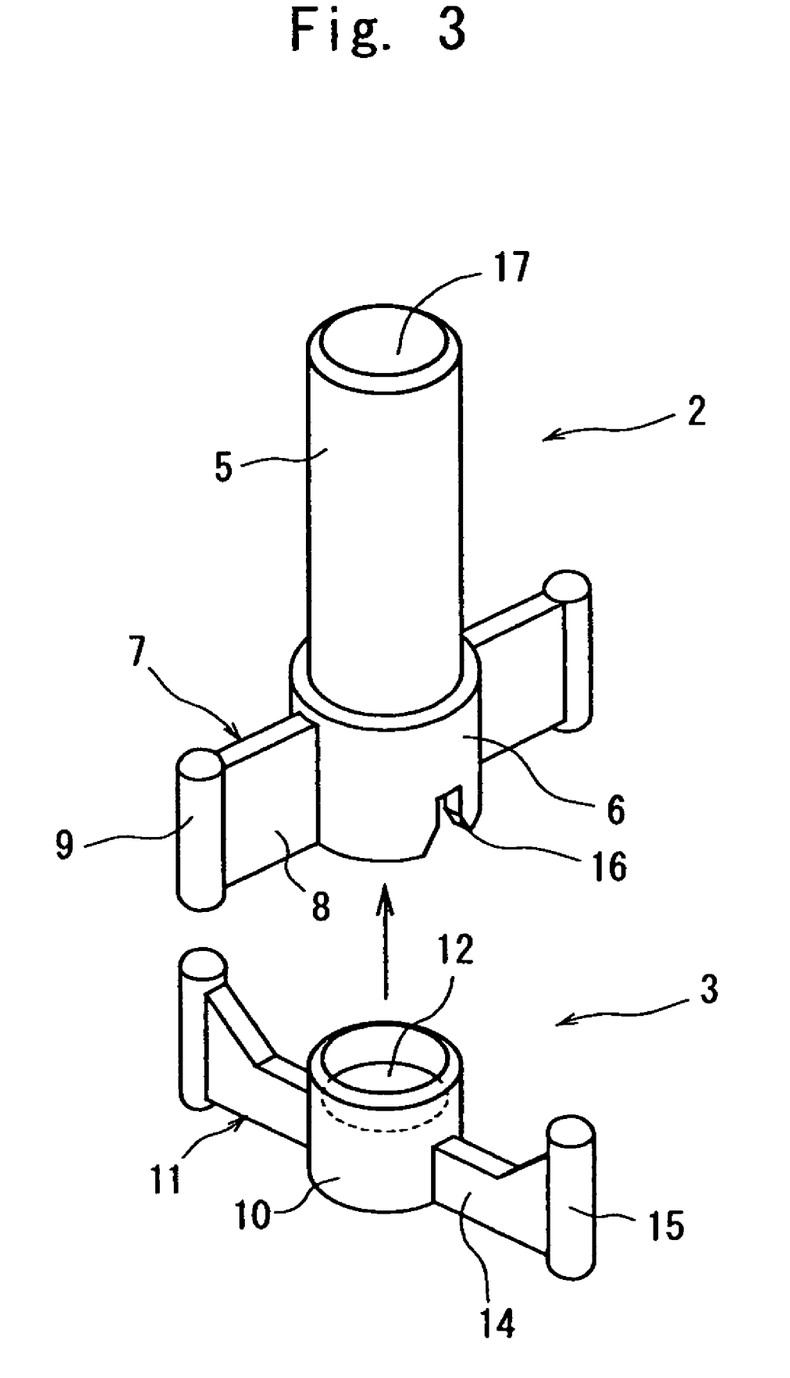
FIG. 3 is a perspective view of the container in a state where the lid member is removed from the container body of FIG. 1 and is going to be fitted to the container body.
Figure 4:
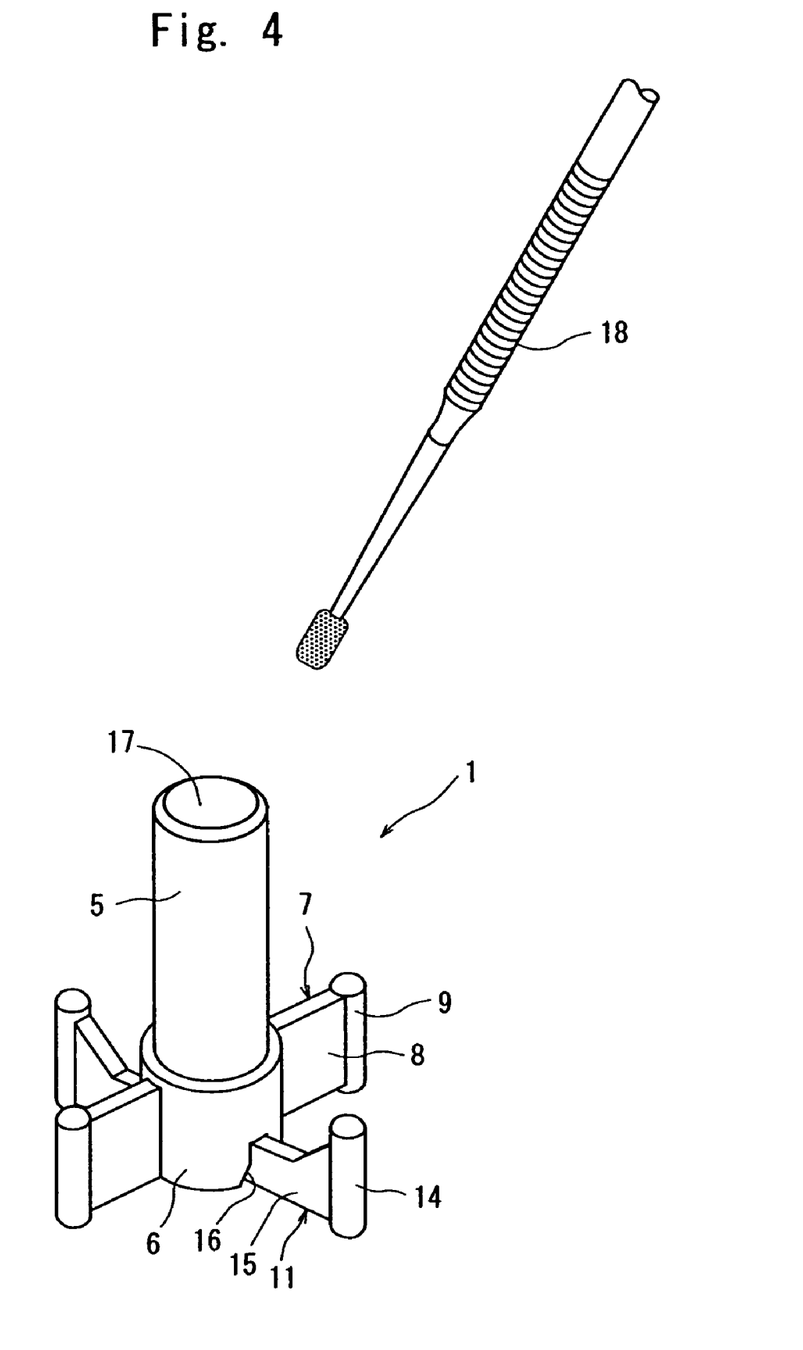
FIG. 4 is a perspective view of the container in a state where the lid member is removed from the container body of FIG. 1 and is fitted to the container body.

After the lid member 3 is separated from the container body 2, the holding leg members 11 are directed upside down as shown in FIG. 3. Besides, the positions of the holding leg portions 11 of the lid member 3 are turned in the circumferential direction by 90 degrees with respect to the auxiliary leg portions 7 of the container body 2. The lid member 3 is brought to just under the pedestal 6 of the container body 2, the lid body 10 of the lid member 3 is fitted into the inner hole of the pedestal 6, and the wing portions 14 of the holding leg portions 11 are inserted in the slits 16. As shown in FIG. 4, therefore, the container body 2 and the lid member 3 are coupled together in the shape of a rocket, and the lower portion of the container 1 acquires a cross shape relying on the auxiliary leg portions 7 and the holding leg portions 11.

Therefore, upon being placed on a suitable position in a state where the take-out opening 17 of the container body 2 is facing upward, the container 1 maintains an erected attitude with stability. In fitting the lid member 3 to the container body 2, the slits 16 serve as positioning portions enabling the leg portions 7 and 11 to be reliably formed in a cross shape.

The dentist inserts an end of a rod 18 in the take-out opening 17 of the container 1 which is placed maintaining stability and takes out the adhesive, preventing such an occurrence that the container falls down while taking out the adhesive.

The container 1 according to the embodiment is designed in the shape of a rocket as described above and, therefore, the cylindrical portions 15 may not be formed on the outer sides at the ends of the auxiliary leg portions 7 and holding leg portions 11. Or, the holding members may be formed in quite another shape.

Therefore, the dentist is allowed to apply the adhesive to the patient's teeth by using both hands while the container body 2 is stood on a suitable place. After the therapy, the container 1 is discarded. Here, however, the container body 2 and the lid member 3 are coupled together, and are not separately discarded. Usually, the lid member 3 turns into garbage at a moment when it is separated away from the container body 2. According to the present invention, however, the lid member 3 can be effectively utilized before it turns into garbage.

When the auxiliary leg portions 7 and the holding leg portions 11 are fitted together in the cross shape as shown in FIG. 4, the longitudinal and transverse lengths are L×L (as for L, see FIG. 1). In a state where the container 1 is not still used, however, the longitudinal and transverse lengths are L×W (as for W, see FIG. 2). When many containers 1 that have not been used are to be packed in a box, therefore, the thickness of the whole shape of each container 1 can be decreased. Upon, for example, horizontally stacking the containers 1, therefore, an increased number of the containers 1 can be contained in a package of a decreased volume.

Next, described below is a second embodiment of the present invention.

The same portions as those of the above first embodiment are denoted by the same reference numerals but their detailed description is not repeated.

In the above first embodiment as shown in FIG. 1, two auxiliary leg portions 7 are formed on the side of the container body 2, and the holding leg portions 11, too, are similarly formed in a number of two on the lid member 3. However, the numbers of the auxiliary leg portions 7 and holding leg portions 11 may be suitably varied.

Figure 5:
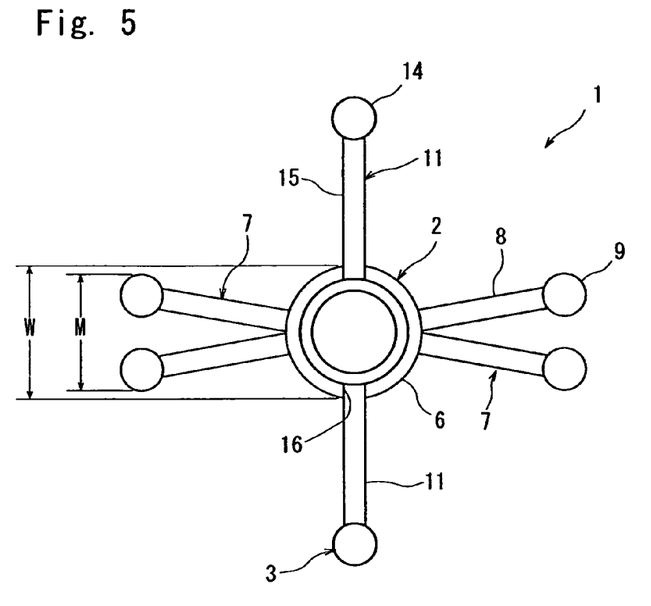
FIG. 5 is a sectional view of a pedestal portion of the container body according to a second embodiment of the invention.

FIG. 5 is a sectional view of the pedestal portion 6 of the container body 2. In this embodiment, four auxiliary leg portions 7 are formed on the outer circumferential portion of the pedestal 6. Two sets of auxiliary leg portions 7 are arranged being opposed to each other in the direction of diameter of the pedestal 6, each set of auxiliary leg portions 7 being close to each other. Here, a maximum distance M at the distal ends of each set of auxiliary leg portions 7 must be smaller than the outer diameter W of the pedestal 6. The lid member 3 has the same shape as that of the lid member 3 of the above embodiment.

The lid member 3 of the same shape as that of the first embodiment is fitted to the pedestal 6; i.e., the container body 2 is maintained in an erected attitude by a total of six leg portions 7 and 11 including four auxiliary leg portions 7 and two holding leg portions 11. Therefore, the container body 2 is maintained in the erected attitude more stably.

In a state where the container body 2 is fell down, the maximum distance M at the distal ends of the auxiliary leg portions 7 is smaller than the outer diameter W of the pedestal 6. Therefore, many containers 1 can be packed requiring substantially the same volume as that of the above first embodiment.

The lid member 3, too, may be provided with four holding leg portions 11 along the circumference thereof in the same structure as that of the auxiliary leg portions 7 of the pedestal 6. In this case, the container body 2 can be further stabilized to maintain the erected attitude.

The container according to a third embodiment of the invention will be described below with reference to the drawings.

Figure 6:
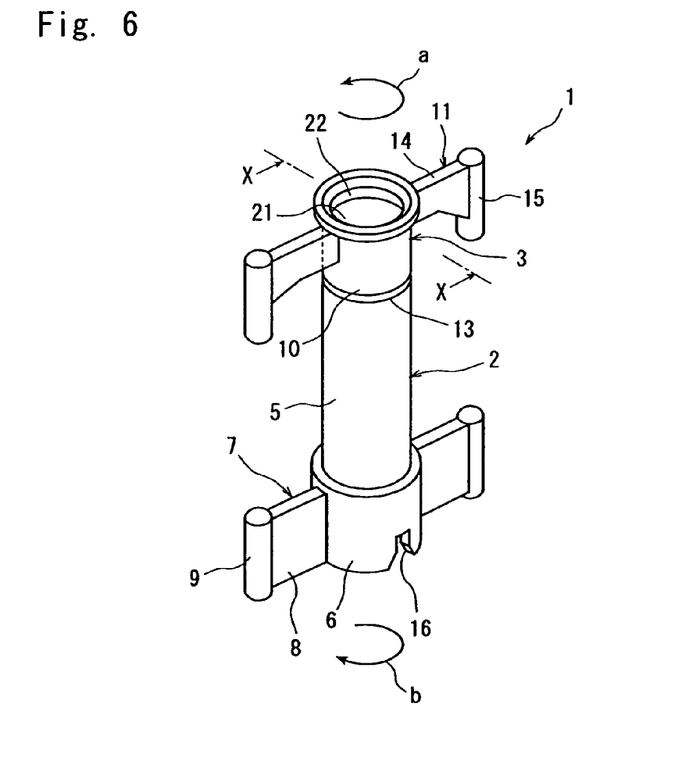
FIG. 6 is a perspective view of the container comprising the container body and the lid member according to a third embodiment of the invention in a state where the container is still unsealed.

FIG. 6 is a perspective view of the container containing an adhesive for dental therapy in a state of not yet used as viewed from the upper side.

As shown, the container 1 is a so-called disposable container for containing an adhesive for dental therapy. The plastic container 1 made of a plastic material includes a container body 2 formed in the lower portion and a lid member 3 of the same material as the container body 2 formed in the upper portion.

The container body 2 forms a body portion 5 in the upper portion thereof for containing an adhesive, and the body portion 5 is of a cylindrical shape with bottom. In the lower portion of the body portion 5, a pedestal 6 is formed having a diameter larger than that of the body portion 5. Two auxiliary leg portions 7 are formed surrounding the pedestal 6, opposed to each other in the radial direction of the pedestal 6, protruding outward in the direction of diameter, and facing the center of the pedestal 6. The auxiliary leg portions 7 include wing portions 8 coupled at the ends on one side to the pedestal 6 and cylindrical portions 9 coupled to the ends on the other side of the wing portions 8. The wing portions 8 are plate members of a square shape, and the upper ends of the cylindrical portions 9 are protruding beyond the upper ends of the wing portions 8.

Figure 7:
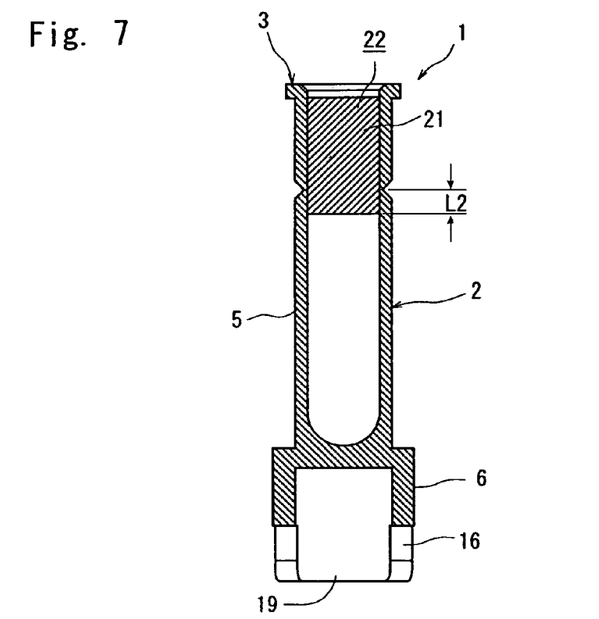
FIG. 7 is a sectional view in the direction of X-X line in FIG. 6.

The lid member 3 shown in FIG. 6 includes the lid body 10 and holding leg portions 11. Referring to FIG. 7, the cylindrical lid body 10 is formed having an outer diameter which is the same as the inner diameter of the container body 2. The junction portion between the lid body 10 and the container body 2 is forming a brittle portion 13. The brittle portion 13 may be formed by integrally forming the lid body 10 and the container body 2 together, and forming a thin portion therebetween, or may be formed by forming the lid body 10 and the container body 2 separately from each other and, thereafter, joining the lid body 10 and the container body 2 together with an adhesive. In this embodiment, the lid body 10 and the container body 2 are separately formed and are, thereafter, joined together by heat-melt adhesion.

The holding leg portions 11 are formed in a number of two surrounding the lid body 10, facing in the radial direction of the lid body 10 and protruding outward in the direction of diameter. The holding leg portions 11 include wing portions 14 coupled at the ends on one side to the lid body 10 and cylindrical portions 15 coupled to the ends on the other side of the wing portions 14. The positions where the holding leg portions 11 are formed are at the same circumferential angular positions as those of the plate surface of the auxiliary leg portions 7 of the container body 2.

The closing member 21 is made from a nearly cylindrical elastic member which is a synthetic resin. In this embodiment, the closing member 21 has an outer diameter which is larger than the inner diameters of the lid member 10 and the container body 2. Referring to FIG. 7, further, the position where the closing member 21 is arranged is such that one end of the closing member 21 protrudes by a length L2 toward the container body 2 beyond the brittle portion 13 between the lid body 10 and the container body 2. In a state where the closing member 21 is fitted to the lid body 10, therefore, the closing member 21 is compressed in the radial direction and pushes the inner circumferential surfaces of the lid body 10 and the container body 2 due to its repulsive force.

Figure 8:
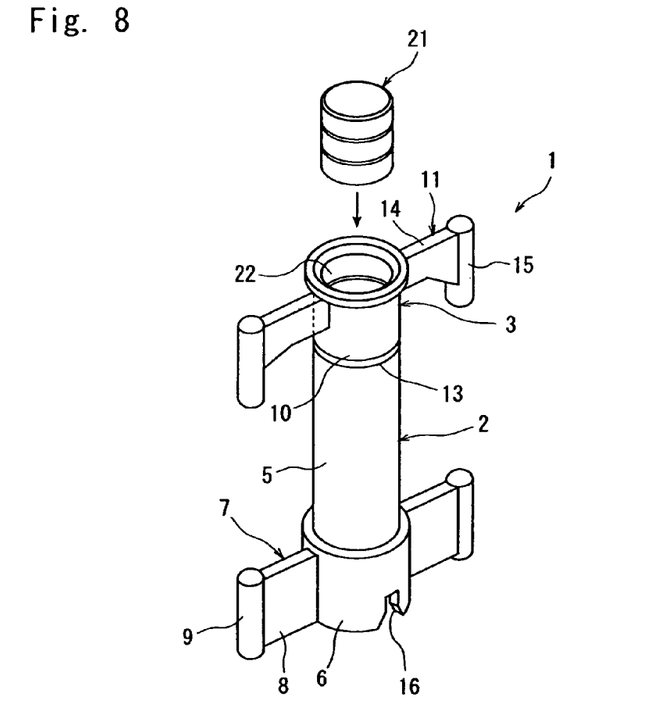
FIG. 8 is a perspective view of before fitting a closing member into the container of FIG. 6.

To fit the closing member 21 to the lid body 10, the lid body 10 and the container body 2 are melt-adhered together as shown in FIG. 8. Thereafter, the content (adhesive for medical use) is contained in the container 1, and the closing member 21 is pushed into the opening 22 of the lid body 10 so as to extend across the brittle portion 13. No particular adhesive is required for fixing the closing member 21, and the closing member 21 is fixed in the container 1 due to the repulsive force stemming from the elastic force of the closing member 21.

The pedestal 6 of the container body 1 is of a cylindrical shape having bottom with its lower side open. A pair of slits 16 is formed in the circumferential wall of the pedestal 6 extending upward from the lower end of the circumferential wall. The positions where the slits 16 are formed are arranged on a line at right angles with a line that connects the pair of auxiliary leg portions 7 passing through the center of the pedestal 6. Therefore, the auxiliary leg portions 7 and the slits 16 are alternately arranged in the circumferential direction of the pedestal 6 at an angle of 90 degrees. The width of the slit 16 is nearly equal to the thickness of the wing portion 14 of the holding leg portion 11.

Figure 9:
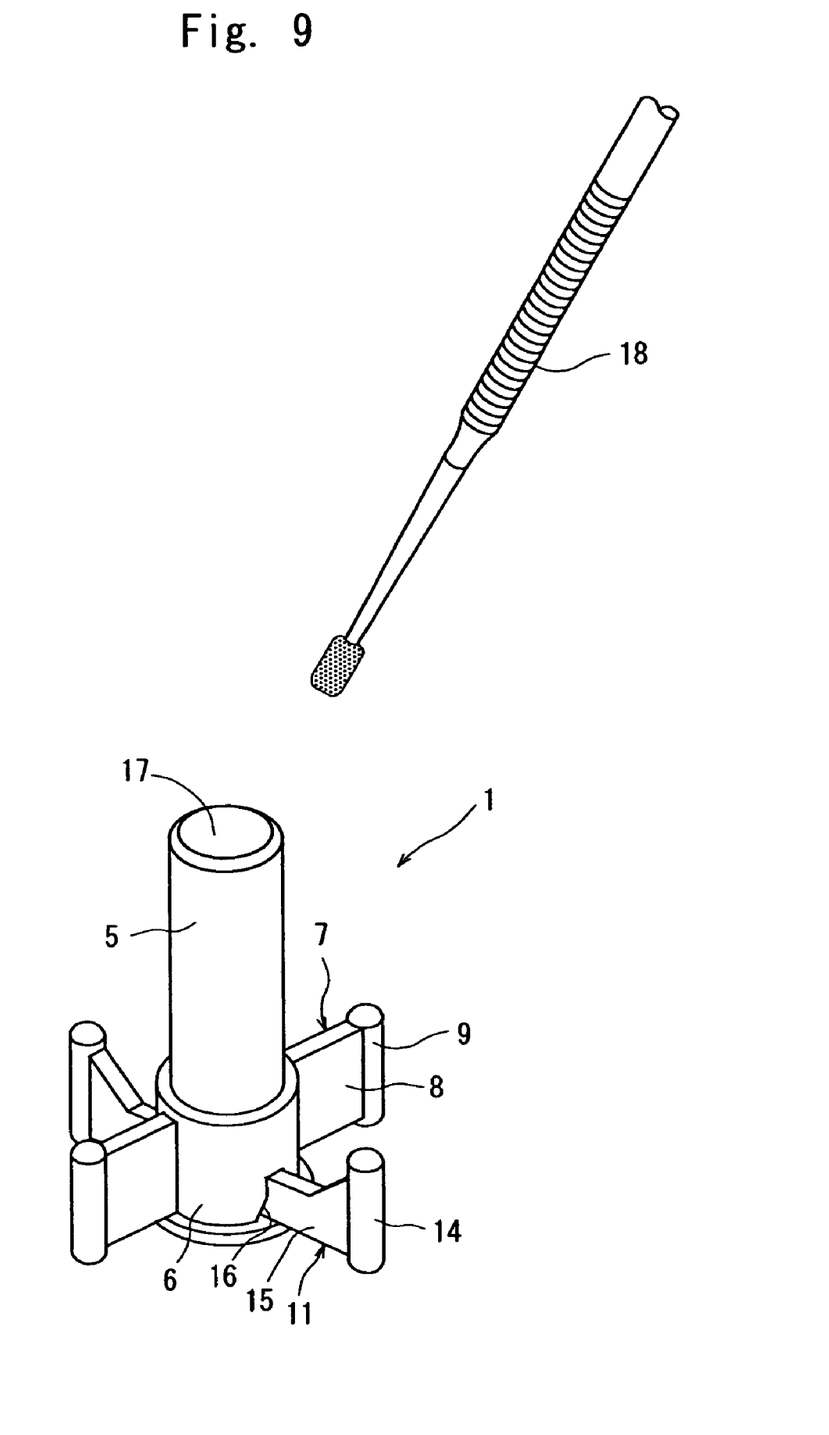
FIG. 9 is a perspective view of the container in a state where the lid member is removed from the container body and is fitted to the container body.

Referring to FIG. 7, an inner hole 19 (see also the inner hole 19 of FIG. 2) is formed in the pedestal 6, the inner hole 19 having an inner diameter nearly equal to the outer diameter of the lid body 10 of the lid member 3. The lid member 3 that is separated from the container body 2 can be fitted into the inner hole 19 of the pedestal 6 as shown in FIG. 9.

A dentist who is going to treat the teeth may use an adhesive contained in the above container. Namely, he may grip the auxiliary leg portions 7 of the container body 2 by his one hand, grip the holding leg portions 11 of the lid member 3 by his other hand, and may turn the auxiliary leg portions 7 of the container body 2 and the holding leg portions 11 in the opposite directions as indicated by arrows a and b in FIG. 6 to break the brittle portion 13. Here, the brittle portion 13 has no elasticity and, therefore, the lid body 10 and the container body 2 can be instantaneously separated from each other.

The lid body 10 and the container body 2 are turned in the circumferential directions, and no force acts in a direction in which the container body 2 is pulled out in the axial direction. Even if they are in a broken state, the closing member 21 is extending across the brittle portion 13. Therefore, the closing member 21 plays the role of a coupling member as it pushes the inner circumferential surface of the container body 2, and the lid member 3 and the container body 2 are maintained in a state of being coupled together.

That is, the container body 2 and the lid member 3 can be smoothly turned in the opposite directions with the closing member 21 as a rotary shaft suppressing the movement of the container body 2. Therefore, the opening 17 of the container body 2 swings little, and the content is greatly suppressed from swinging. Besides, even if the container body 2 moves to some extent, the opening 17 of the container body 2 is maintained in a state of being closed by the closing member 21 preventing the content from flying out of the container body 2.

Here, the holding leg portions 11 have a large distance between the cylindrical portions 15 and 15 at both ends, and produce a large moment of rotation enabling the brittle portion 13 to be cut with a small force.

After the lid member 3 is separated from the container body 2, the lid member 3 is directed upside down, and the positions of the holding leg portions 11 of the lid member 3 are turned in the circumferential direction by 90 degrees with respect to the auxiliary leg portions 7 of the container body 2. The lid member 3 is brought to just under the pedestal 6 of the container body 2, the lid body 10 of the lid member 3 is fitted into the inner hole of the pedestal 6, and the wing portions 14 of the holding leg portions 11 are inserted in the slits 16. As shown in FIG. 9, therefore, the container body 2 and the lid member 3 are coupled together in the shape of a rocket, and the lower portion of the container 1 acquires a cross shape relying on the auxiliary leg portions 7 and the holding leg portions 11 enabling the container 1 to be placed on any place maintaining stability.

As described above, the container 1 that is placed on a suitable position stably maintains the erected attitude with the take-out opening 17 of the container body 2 being faced upward.

Therefore, the dentist is allowed to take out the adhesive by inserting the end of the rod 18 in the take-out opening 17 of the container 1 that is placed in a stable state. If the dentist does not all use the adhesive and desires to use again the adhesive that is left, then the closing member 21 may be inserted in the opening 17 of the container body 2 and the lid member 3 may be fitted to the container body 2 to preserve the adhesive.

As described above, the closing member 21 plays the role of a closing plug and is, further, arranged extending across the brittle portion 13. Therefore, the interior of the container 1 is maintained closely adhered though the coupling portion has not been so closely adhered.

Next, described below is a forth embodiment of the invention.

Here, however, the same portions as those of the above embodiments are denoted by the same reference numerals.

Figure 10:
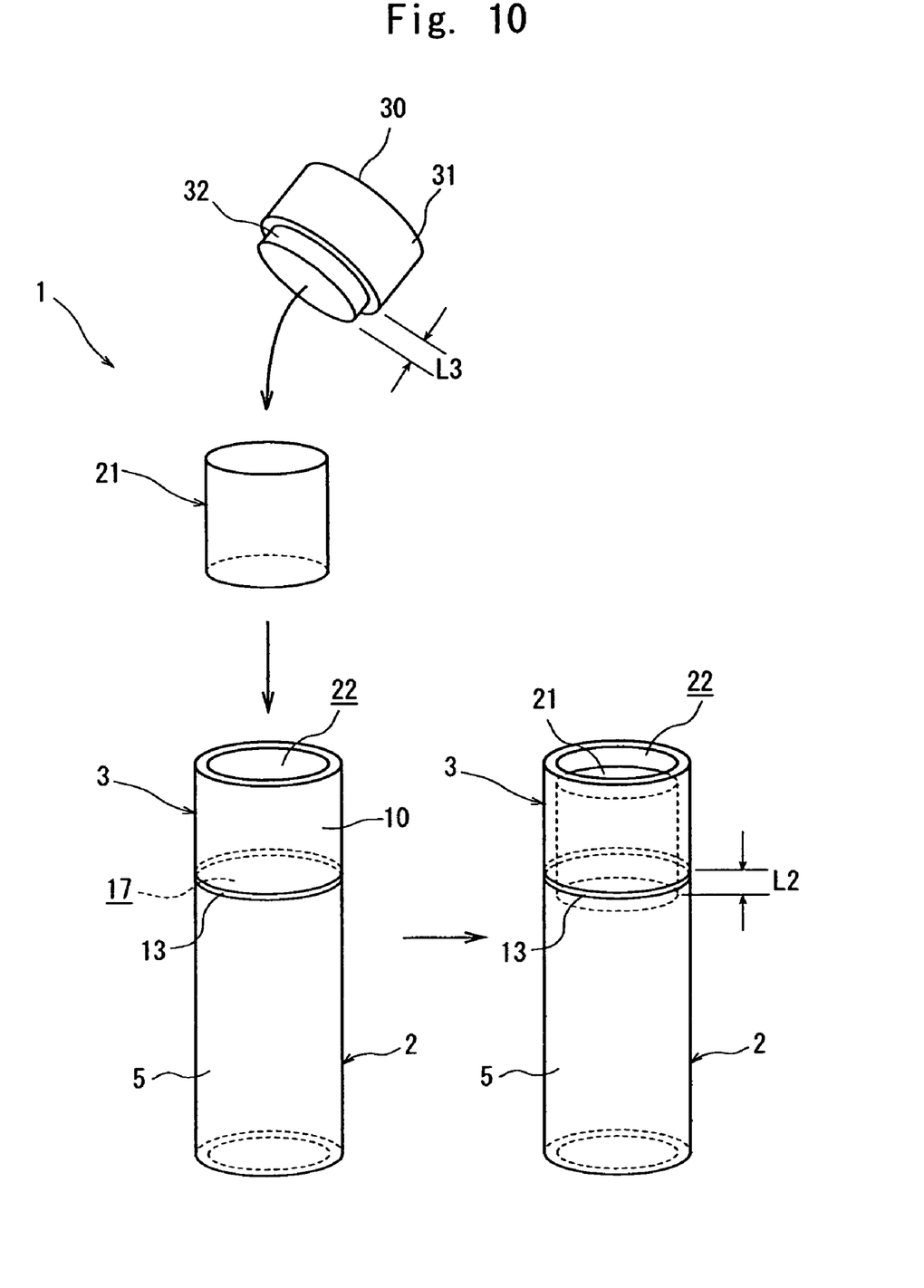
FIG. 10 shows a disassembled perspective view of the container and a perspective view of the container according to a fourth embodiment of the invention.

Referring to FIG. 10, the container 1 is a so-called general-purpose container which is not limited to the one for containing an adhesive for dental use, and is capable of containing a liquid, a powder or a granular solid.

The container 1 made of a plastic material includes the plastic container body 2 formed in the lower portion and the lid member 3 of the same material as the container body 2 and is formed in the upper portion.

Of them, the container body 2 is of a cylindrical shape with bottom. The lid member 3 includes the lid body 10 and the cylindrical closing member 21, the lid member 10 having an outer diameter which is the same as the inner diameter of the container body 2. The junction portion between the lid body 10 and the container body 2 is forming the brittle portion 13. The brittle portion 13 may be formed by integrally forming the lid body 10 and the container body 2 together, and forming a thin portion therebetween, or may be formed by forming the lid body 10 and the container body 2 separately from each other and, thereafter, joining the lid body 10 and the container body 2 together with an adhesive. In this embodiment, the lid body 10 and the container body 2 are separately formed and are, thereafter, joined together by heat-melt adhesion.

The closing member 21 is made from a nearly cylindrical elastic member which is a synthetic resin. Here, the closing member 21 has an outer diameter which is larger than the inner diameters of the lid body 10 and the container body 2. The position where the closing member 21 is arranged is such that one end of the closing member 21 protrudes by a length L2 toward the container body 2 beyond the brittle portion 13 between the lid body 10 and the container body 2. In a state where the closing member 21 is fitted to the lid body 10, therefore, the closing member 21 is compressed in the radial direction and is fitted in the container 1.

Use of a jig 30 is convenient for fitting the closing member 21 to the container 1. The jig 30 includes a stopper 31 and a pushing portion 32 which is a protuberance. If the pushing portion 32 of the jig 30 has a length L3 so that the closing member 21 protrudes beyond the brittle portion 13 by a length L2, then the closing member 21 can be easily pushed by a correct amount. After the brittle portion 13 is broken, therefore, the closing member 21 closes the opening 17 of the container body 2 with a predetermined closing force or with a closing force which lies in a predetermined range.

Even in the container 1 of a general shape as described above, the closing member 21 is closing the opening 17 of the container body 2 when the brittle portion 13 is broken preventing the content from flying out of the container body 2. Further, the closing member 21 is made of an elastic member and is closing the container body 2 over a small length. Therefore, the closing member 21 can be easily removed from the container body 2 by pulling out the lid member 3.

The container of the present invention is such that after the container body and the lid member are separated from each other, the lid member is fitted to the engaging portion of the container body, and the container body maintains its erected attitude relying on the holding portions. Therefore, the container can be held maintaining stability so will not to fall down. Here, it is not important that the container body of the container by itself can maintain an erected attitude.

The container body of the container is forming auxiliary portions protruding outward from the body portion of the container body and maintains the erected attitude relying on the holding portions and the auxiliary portions. Therefore, the container body stably maintains the erected attitude.

In a state where the container body is still unsealed, the holding portions of the lid member of the container and the auxiliary portions are so arranged as to pass on the same horizontal plane and in a state where the lid body is fitted, the holding portions and the auxiliary portions are arranged in nearly a cross shape enabling the container body to more stably maintain the erected attitude. Further, the lid member can be unsealed with a small torque by turning the holding portions.

The lid member of the container is provided with three or more holding leg portions. In a state where the cap body is falling down, the height of the holding leg portion which is the highest among the three or more holding leg portions is set to be smaller than a maximum width or a maximum diameter of the body portion. When many containers are collectively packed, therefore, the height of the holding leg portion does not become larger than the thickness of the body portion, making it possible to decrease the packing volume.

The lid member of the container and the container body are integrally coupled together at the take-out opening portion relying on the brittle portion that can be broken. Usually, therefore, the lid member after broken is discarded separately from the container body. According to the present invention, however, the lid member and the container body are discarded being coupled together instead of being separated away from each other. Further, the lid member is functionally used as a holding portion for holding the container body before being discarded.

In the container of the present invention, the coupling portion between the lid member and the container body is provided with the closing member that protrudes toward the container body side, and the opening portion of the container body is closed by the closing member. At the time of breaking the lid member from the container body, therefore, the container body and the lid member can be smoothly turned in the opposite directions with the closing member as the rotary shaft suppressing the motion of the container body. Therefore, the opening of the container body swings little greatly suppressing the content from swinging. Even if the container body moves to some extent, the opening of the container body is maintained closed by the closing member preventing the content from flying out of the container body. Even if the brittle portion is not air-tight, the brittle portion is coupled by the closing member and, therefore, the container body is maintained air-tight irrespective of the air-tightness of the brittle portion.

The above container comprises the cylindrical portion in which the lid member is coupled to the opening portion and the closing member that is arranged in the inner circumferential portion of the cylindrical portion, the closing member being inserted in the cylindrical portion of the lid member. After the container body and the lid member are joined together, therefore, the closing member is fitted. Namely, they can be joined together prior to introducing the content into the container body.

In the above container, the closing member is made of an elastic member having an outer circumferential surface which in cross section is larger than the inner circumferential surface of the cylindrical portion in cross section. Therefore, the closing member stably maintains the closely adhering force. Even after the lid member is separated away from the container body, the closing member stably maintains closed the opening portion of the container body.

The container body of the container is forming grip portions protruding outward from the outer circumferential surface of the container body while the lid member is forming grip portions protruding outward from the outer circumferential surface of the lid member, and the cutting portion is cut by turning the pair of grip portions in the opposite directions. Therefore, the container body and the lid member can be easily broken apart requiring a further decreased force.

The content to be introduced into the container body of the container is an adhesive for medical use. At the time of unsealing, therefore, the adhesive for medical use that tends to easily fly out can be prevented from flying out of the container.

Though the invention was described above by way of embodiments, it should be noted that the invention can be modified or altered in a variety of other ways without departing from the technical scope of the invention.

For example, the above embodiments have dealt with the dental container for containing an adhesive for dental use. However, the container is not limited to the dental use only but can also be applied to other containers that need to be stably erected.

In the above embodiments, the lid body 10 is internally fitted in the inner hole 19 of the pedestal 6. The lid body 10, however, may be externally fitted to the outer circumferential portion of the pedestal 6. In this case, slits are formed in the lid body 10 so that the wing portions 8 of auxiliary leg portions 7 of the pedestal 6 can be inserted in the slits. In this case, the container body 2 can be utilized down to the bottom portion thereof for containing the content. Moreover, the height of the container body can be decreased and, therefore, the erected attitude of the container body 10 can be further stabilized.

In the above embodiments, the container body 2 and the lid member 3 were coupled together relying on the brittle portion 13 which was designed to be broken. The lid member 3, however, may be of a threaded type or an insertion (fit) type.

Further, if the size of the package is not of a problem, the lid member 3 may be provided with the portions corresponding to the auxiliary leg portions 7, so that the lid member 3 possesses the leg portions 7, 11 arranged in a cross shape in addition to the existing holding leg portions 11.

Figure 11:
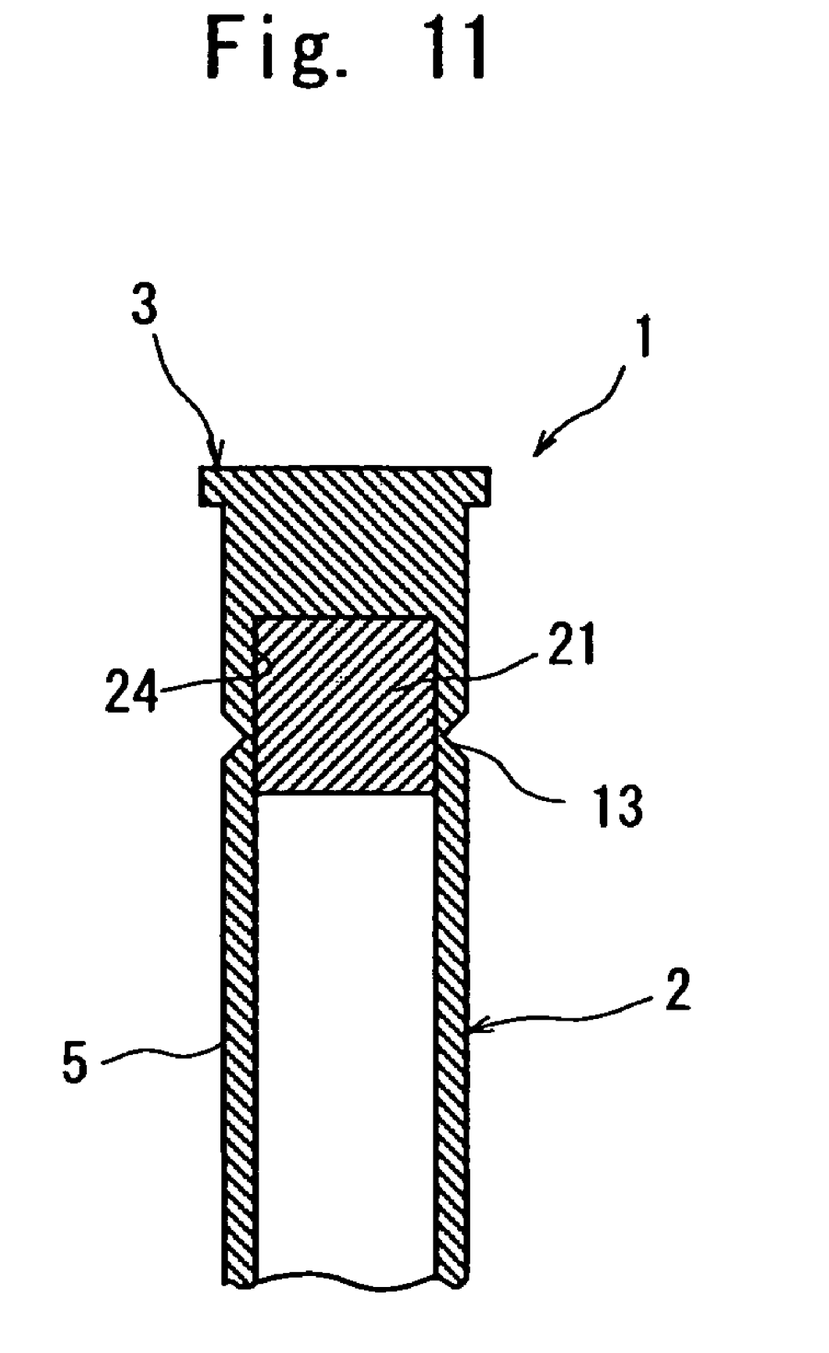
FIG. 11 is a sectional view of the container according to a modified embodiment of the invention.

In the above third and fourth embodiments, the lid member 3 was formed in a cylindrical shape, the container body 2 and the lid member 3 were heat-melt adhered together and, thereafter, the closing member 21 was fitted to the lid member 3 and to the container body 2. However, the lid body 10 of the lid member 10 does not have to be of a cylindrical shape, and the lid member 3 having a closed upper end can also be used. That is, as shown in FIG. 11, the lid member 3 forms a fitting portion 24 that fits to the closing member 21 on the side that joins to the container body 2, and the closing member 21 is fitted into the fitting portion 24 to close the container body 2. As shown in FIG. 11, further, the lid body 10 and the closing member 21 may be formed as a unitary structure.

The invention claimed is:

1. A container comprising a container body which is unable to maintain an erected attitude by itself and a lid member for closing one end portion of said container body, wherein
    said container body has, formed at another end portion thereof, an engaging portion for fitting said lid member to said container body,
    said lid member has, formed therein, a lid body for closing said container body and two holding leg portions which consist of plate-like wing portions protruding outward in the direction of diameter beyond a body portion of said container body that contains the content therein,
    two auxiliary leg portions which consist of plate-like wing portions are so formed at a lower portion of said container body as to protrude outward in the direction of diameter beyond the body portion of said container body;

said holding leg portions are arranged at positions facing each other on a straight line passing through the central portion of said lid body, said auxiliary leg portions are arranged at positions facing each other on a straight line passing through the central position of said container body, said engaging portion of said container body comprises slits which are so formed as to extend upward from the lower end of the container body, and to maintain said container body in an erected attitude, said container body and said slits are configured to receive said lid body and said holding leg portions, respectively, and said holding leg portions and said auxiliary leg portions are protruded outward in the direction of diameter beyond the lid body and the container body, respectively.

2. The container according to claim 1, wherein said holding leg portions and said auxiliary leg portions being arranged so as to pass through a common horizontal plane in a state where said container body is still unsealed, and said holding leg portions and said auxiliary leg portions being arranged nearly in a cross shape in a state where said lid body is fitted to the engaging portion of said container body.

3. The container according to claim 1, wherein said lid member and said container body are integrally coupled together at a take-out opening portion, the coupling being attained relying on a thin portion that can be broken, and the content in said container body is an adhesive for dental use.

* * * * *